US011122796B1

(12) United States Patent
Manuchehrabadi et al.

(10) Patent No.: US 11,122,796 B1
(45) Date of Patent: Sep. 21, 2021

(54) CRYOPROTECTION COMPOSITIONS AND METHODS

(71) Applicant: REGENTS OF THE UNIVERSITY OF MINNESOTA, Minneapolis, MN (US)

(72) Inventors: Navid Manuchehrabadi, Minneapolis, MN (US); Meng Shi, Xi'an (CN); Feng Xu, Xi'an (CN); TJ Lu, Xi'an (CN); John Bischof, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 22 days.

(21) Appl. No.: 15/999,315

(22) PCT Filed: Feb. 17, 2017

(86) PCT No.: PCT/US2017/018331
§ 371 (c)(1),
(2) Date: Aug. 17, 2018

(87) PCT Pub. No.: WO2017/143162
PCT Pub. Date: Aug. 24, 2017

Related U.S. Application Data

(60) Provisional application No. 62/297,527, filed on Feb. 19, 2016.

(51) Int. Cl.
*A01N 1/02* (2006.01)
*C12N 13/00* (2006.01)

(52) U.S. Cl.
CPC ......... *A01N 1/0268* (2013.01); *A01N 1/0284* (2013.01); *C12N 13/00* (2013.01)

(58) Field of Classification Search
CPC .................................................. A01N 1/0268
See application file for complete search history.

(56) References Cited

U.S. PATENT DOCUMENTS

| | | | |
|---|---|---|---|
| 5,328,821 A | 7/1994 | Fisher et al. | |
| 5,660,076 A | 8/1997 | Jonkka et al. | |
| 5,780,295 A | 7/1998 | Livesey et al. | |
| 6,381,967 B1 | 5/2002 | Craig | |
| 7,112,576 B1 | 9/2006 | Hubel | |
| 8,790,923 B2 | 7/2014 | Ennis et al. | |
| 2005/0016198 A1 | 1/2005 | Wowk | |
| 2009/0133410 A1 | 5/2009 | Thorne et al. | |
| 2010/0003197 A1 | 1/2010 | Bikram | |
| 2010/0317108 A1 | 12/2010 | Stojanov | |
| 2011/0207112 A1 | 8/2011 | Burbank et al. | |
| 2012/0087868 A1 | 4/2012 | Todd et al. | |
| 2012/0276334 A1 | 11/2012 | Fedynyshyn et al. | |
| 2015/0351381 A1 | 12/2015 | Vom et al. | |
| 2016/0015025 A1 | 1/2016 | Bischof | |
| 2017/0350798 A1 | 12/2017 | Carragher | |
| 2018/0192639 A1 | 7/2018 | Brockbank et al. | |

FOREIGN PATENT DOCUMENTS

| | | |
|---|---|---|
| CN | 101744766 A | 6/2010 |
| CN | 102835389 A | 12/2012 |
| CN | 104782616 A | 7/2015 |
| CN | 104012521 B | 8/2015 |
| CN | 104396942 A | 3/2016 |
| EP | 2381226 A1 | 10/2011 |
| JP | 2011231021 A | 11/2011 |
| WO | WO 98/10231 A1 | 3/1998 |
| WO | 2007077560 A2 | 7/2007 |
| WO | 2014/085801 A1 | 6/2014 |
| WO | WO 2014/143961 A1 | 9/2014 |
| WO | 20170184721 A1 | 10/2017 |
| WO | 2018/073242 A1 | 4/2018 |

OTHER PUBLICATIONS

Bearer et al., J Electron Microsc Tech., 1986, 3(2):233-241.*
International Patent Application No. PCT/US17/18331, filed Feb. 17, 2017; International Search Report / Written Opinion dated May 8, 2017; 9 pages.
International Patent Application No. PCT/US17/18331, filed Feb. 17, 2017; International Preliminary Report on Patentability dated Aug. 30, 2018; 7 pages.
Baicu, "Vitrification of carotid artery segments: an integrated study of thermophysical events and functional recovery toward scale-up for clinical applications" 2006 Cell Preserv. Technol. 4(4):236-244.
Brockbank, Vitrification of Heart Valve Tissues. Springer: New York, NY; 2015. Cover page, title page, table of contents, and pp. 399-421.
Burdette, Kidney model for study of electromagnetic thawing. Cryobiology 15(2):142-151, 1978.
Burdette, "Microwave thawing of frozen kidneys: a theoretically based experimentally-effective design" 1980 Cryobiology 17(4):393-402.
Eisenberg, "Stress-Strain Measurements in Vitrified Arteries Permeated With Synthetic Ice Modulators" *J Biomech Eng*. Aug. 2015.
Eisenberg, "Thermomechanical Stress in Cryopreservation Via Vitrification With Nanoparticle Heating as a Stress-Moderating Effect" *J Biomech Eng*. Dec. 2015.
Eisenberg, "On the effects of thermal history on the development and relaxation of thermo-mechanical stress in cryopreservation" 2014 Cryogenics (Guildf) 33(4):395-401.
Elliott, "Cryoprotectants: a review of the actions and applications of cryoprotective solutes that modulate cell recovery from ultra-low temperatures" 2017 Cryobiology 76:74-91.
Etheridge, "Optimizing Magnetic Nanoparticle Based Thermal Therapies Within the Physical Limits of Heating" 2013 *Annals of Biomedical Engineering* 41(1):78-88.
Etheridge, "RF heating of magnetic nanoparticles improves the thawing of cryopreserved biomaterials" 2014 *Technology*, 2(03):229-242.

(Continued)

*Primary Examiner* — Bin Shen

(74) *Attorney, Agent, or Firm* — Westman, Champlin & Koehler, P.A.; Visala C. Goswitz

(57) ABSTRACT

Compositions and methods for cryoprotecting a biological tissue can involve a cryoprotective agent and a metal component that includes a metal foam, a metal foil, or a metal seed. The method allows the biological tissue to be rewarmed at a rate of at least 100° C./min.

20 Claims, 15 Drawing Sheets

(56) References Cited

OTHER PUBLICATIONS

Evans, "Electromagnetic rewarming: the effect of CPA concentration and radio source frequency on uniformity and efficiency of heating" 2000 Cryobiology 40(2): 126-138.
Fahy, "Vitrification as an approach to cryopreservation" 1984 *Cryobiology*, 21(4): 407-26.
Fahy, "Cryopreservation of complex systems: the missing link in the regenerative medicine supply chain" 2006 Rejuvenation Res. 9(2):279-291.
Giwa, "The promise of organ and tissue preservation to transform medicine" 2017 Nat. Biotechnol. 35(6):530-542.
Hahn, *Heat Conduction*. Wiley: Hoboken, NJ; 2012. Cover page, title page, table of contents.
Incropera, Fundamentals of Heat and Mass Transfer. Hoboken: Wiley, 1996. Cover page, title page and table of contents.
Karlsson, "Long-term storage of tissues by cryopreservation: critical issues" 1996 *Biomaterials* 17(3):243-256.
Lewis, "The Grand Challenges of Organ Banking: proceedings from the first global summit on complex tissue cryopreservation" 2016 *Cryobiology* 72(2):169-182.
Luo "Development of a single mode electromagnetic resonant cavity for rewarming of cryopreserved biomaterials" 2006 *Cryobiology*, 53(2006):288-293.
Manuchehrabadi, "Ultrarapid Inductive RF Metal Foam Rewarming of Vitrified Biomaterials for Regenerative Medicine" Nov. 2018 *Annals of Biomedical Eng.*, 46(11):1857-1869.
Manuchehrabadi, "Improved tissue cryopreservation using inductive heating of magnetic nanoparticles" 2017 *Sci. Transl. Med.* 9(379):eaah4586.
Mazur, "Freezing of living cells: mechanisms and implications" 1984 *Am. J. Physiol.* 247(3 Pt 1):C125-C142.
Mehl, "Nucleation and Crystal Growth in a Vitrification Solution Tested for Organ Cryopreservation by Vitrification" 1993 *Cryobiology*, 30(5):509-518.
Noday, "Viscosity of cryoprotective agents near glass transition: a new device, technique, and data on DMSO, DP6, and VS55" 2009 *Cryoletters* 49(5):663-672.
Peyrideu, "Critical Cooling and Warming Rates to Avoid Ice Crystallization in Small Pieces of Mammalian organs Permeated with Cryoprotective Agents" 1996 *Cryobiology*, 33:436-446.
Rabin, "Cryomacroscopy of vitrification, part I: a prototype and experimental observations on the cocktails VS55 and DP6" 2005 *Cell Preserv. Technol.* 3(3):169-183.
Rachman, Electromagnetic Warming of Cryopreserved Organs. Thesis. Cambridge: University of Cambridge, 1990.
Rall, "Ice-free cryopreservation of mouse embryos at—196° C. by vitrification" 1985 *Nature*.
Robinson, "Rapid electromagnetic warming of cells and tissues" 1999 IEEE Trans. Biomed. Eng. 46(12):1413-1424.
Robinson, "Electromagnetic re-warming of cryopreserved tissues: effect of choice of cryoprotectant and sample shape on uniformity of heating" 2002 Phys. Med. Biol. 47(13):2311-2325.
Ruggera, "Rapid and uniform electromagnetic heating of aqueous cryoprotectant solutions from cryogenic temperatures" 1990 *Cryobiology*, 27:465-478.
Sandby-Møller, "Epidermal thickness at different body sites: relationship to age, gender, pigmentation, blood content, skin type and smoking habits" 2003 Acta Derm. Venereol. 83(6):410-413.
Shepherd, "Thickness of human articular cartilage in joints of the lower limb" 1999 *Ann. Rheum. Dis.* 58(1):27-34.
Solanki, "Thermo-mechanical stress analysis of cryopreservation in cryobags and the potential benefit of nanowarming" 2017 Cryobiology 76:129-139.
Stauffer, "Observations on the use of ferromagnetic implants for inducing hyperthermia" 1984 IEEE Trans. Biomed. Eng. 31(1):76-90.
Stauffer, "Magnetic induction heating of ferromagnetic implants for inducing localized hyperthermia in deep-seated tumors" 1984 IEEE Trans. Biomed. Eng. 31(2):235-251, 1984.
Steif, "Can thermal expansion differences between cryopreserved tissue and cryoprotective agents alone cause cracking?" 2009 Cryo Letters 30(6):414-421.
Steif, "Continuum mechanics analysis of fracture progression in the vitrified cryoprotective agent DP6" 2008 J. Biomech. Eng. 130(2):21006.
Steif, "Cryomacroscopy of vitrification, part II: experimental observations and analysis of fracture formation in vitrified VS55 and DP6" 2005 Cell Preserv. Technol. 3(3):184-200.
Taylor, "22 Vitrification in Tissue Preservation: New Developments" in Fuller: Life in the Frozen State. CRC Press: Boca Raton, FL; 2004, 604-641.
Wusteman, "Vitrification of large tissues with dielectric warming: biological problems and some approaches to their solution" 2004 *Cryobiology* 48(2):179-189.
International Search Report and Written Opinion issued for PCT/US2020/013956, dated Jun. 2, 2020.
Manuchehrabadi, "Nanowarming of Tissues", Cryobiology, (Dec. 1, 2016), but presented earlier on Jul. 26, 2016 during meeting CRYO2016), pp. 399-443, XP055386203, DOI: 10.1016/j.cryobiol.2016.09.091.
Rypka, "A novel simplified ultra-rapid freezing technique for cryopreservation of tissue slices", Cryobiology, vol. 52, No. 2 (Apr. 1, 2006), pp. 193-199, XP024943396, DOI: 10.1016/j.cryobiol.2005.10.012.
De Graff, "Cryopreservation of rat precision-cut liver and kidney slides by rapid freezing and vitrification", Cryobiology, vol. 54, No. 1, (Feb. 24, 2007), pp. 1-12, XP005907232, DOI: 10.1016/j.cryobiol.2006.09.002.
Halmagyi, "Cryopreservation of Chrysanthemum morifolium (*Dendranthema grandiflora* Ramat.) using different approaches", Plant Cell Reports, vol. 22, No. 6, (Jan. 1, 2004), pp. 371-375, XP55737332, DOI: 10.1007/S00299-003-0703-9.
Examination Report issued for related EP patent application serial No. 17753905.3, dated Oct. 12, 2020.
Albert, "The effect of temperature and freeze-thaw processes on gold nanorods" Dec. 2009 Nanotechnology 20 (50):505502, 6pgs.
Belete, "Novel aqueous nano-scaled formulations of oleic acid stabilized hydrophobic superparamagnetic iron oxide nanocrystals" Feb. 2013 Drug Development and Industrial Pharmacy, 39(2): 186-196.
Deng, "Rapid electromagnetic rewarming of cryopreserved tissues using nano-magnetoparticlesfeasibility study" 2008 Proceedings of the 2nd International Conference on Integration and Commercialization of Micro and Nanosystems, 427-428.
Etheridge, "Radiofrequency heating of magnetic nanoparticle cryoprotectant solutions for improved cryopreservation protocols" 2013 Cryobiology, 67:398-399.
Frazier, "Effects of Heating Temperature and Dauration by Gold Nanorod Mediated Plasmonic Photothermal Therapy on Copolymer Accululation in Tumor Tissue" 2015 Mol. Pharmaceut., 12:1605-1614.
Goiti, "Effect of magnetic nanoparticles on the thermal properties of some hydrogels" 2007 Polymer Degradation and Stability, 92:2198-2205.
Hou, "Magnetic nanohydroxyapatite/PVA composite hydrogels for promoted osteoblast adhesion and prolyferation" Mar. 2013 Colloids and Surfaces B: Biointerfaces, 103(1):318-325.
Kleinhans, "Physical Parameters, Modeling, and Methodological Details in Using IR Laser Pulses to Warm Frozen or Vitrified Cells Ultra-Rapidly" 2015 Cryobiology, 70(2):195-203.
Moscoso-Londono, "Structural and magnetic behaviour of ferrogels obtained by freezing thawing of polyvinyl alcohoVpoly(acrylic acid)(PAA)-coated iron oxide nanoparticles" Feb. 2, 2013 European Polymer Journal, 49(2);279-289.
Polyak, "High field gradient targeting of magnetic nanoparticle-loaded endothelial cells to the surfaces of steel stents" 2008 PNAS, 105(2), 698-703.
Prow, "Ocular nanoparticle toxicity and transfection of the retina and retinal pigment epithelium" 2008 Nanomedicine: Nanotechnology, Biology and Medicine, 4:340-349.
Said et al. Utility of Magnetic Cell Separation as a Molecular Sperm Preparation Technique, Journal of Andrology, vol. 29, No. 2, Mar./Apr. 2008.

(56) References Cited

OTHER PUBLICATIONS

Wang, "Numerical simulation of the effect of superparamagnetic nanoparticles on microwave rewarming of cryopreserved tissues" Feb. 13, 2014 Cryobiology, 68:234-243.
Yong et al. "Green, biodegradable, underwater superoleophobic wood sheet for efficient oil/water separation." ACS omega 3.2 (Feb. 1, 2018): 1395-1402.
International Search Report / Written Opinion issued for PCT/US17/28351 dated Jul. 7, 2017; 14 pages.
International Preliminary Report on Patentability issued for PCT/US17/28351 dated Oct. 23, 2018; 7 pages.
International Search Report and Written Opinion issued for PCT/US2019/041366, dated Nov. 14, 2019.
International Search Report and Written Opinion issued for PCT/US2020/019692, dated May 22, 2020.

* cited by examiner (A)
PRIOR ART (B)

(C)

(A)

(B)

(B)

(A)

.89-20 PPI   .94-20 PPI   .97-20 PPI   Al foil   VS55   .94-20 PPI (B)

.89-20 PPI   .94-20 PPI   .97-20 PPI   Al foil   VS55   .94-20 PPI

Success · Failure · Cracking (C)

i. Convective warming;   ii. Ultrarapid inductive warming: Place into coil

FIG 13

| PPI | Porosity | Mass (gr) | Volume (cm³) | Density (gr/cm³) | HR (°C/min) | SAR (W/cm3) | Metal structure | SAR(W/g) |
|---|---|---|---|---|---|---|---|---|
| 20.00 | 0.89 | 2.5 | 1.67 | 1.49 | 1980 | 233 | | 156 |
| 20.00 | 0.94 | 0.736 | 1.49 | 0.49 | 1460 | 142 | | 289 |
| 20.00 | 0.97 | 0.365 | 1.5 | 0.24 | 1060 | 89 | | 370 |
| N/A | N/A | 0.79 | 1.62 | 0.48 | 1840 | 200 | | 416 |

CRYOPROTECTION COMPOSITIONS AND METHODS

CROSS-REFERENCE TO RELATED APPLICATION

This application is the § 371 U.S. National Stage of International Application No. PCT/US2017/018331, filed Feb. 17, 2017, which claims priority to U.S. Provisional Patent Application No. 62/297,527, filed Feb. 19, 2016, the disclosures of which are incorporated herein by reference in their entireties.

GOVERNMENT FUNDING

This invention was made with government support under 1336659 awarded by the National Science Foundation. The government has certain rights in the invention.

SUMMARY

This disclosure describes, in one aspect, a composition for cryoprotecting a biological tissue. Generally, the composition includes a cryoprotective agent and a metal component. The metal component can include a metal foam, a metal foil, or a metal seed.

In use, the composition further includes a biological tissue.

In some embodiments, the metal component includes a copper foam.

In some embodiments, the metal component includes an aluminum foil.

In some embodiments, the metal component includes a copper seed, an aluminum seed, or an iron seed.

In certain embodiments, the metal component includes a metal foam having at least 10 pores per inch (PPI).

In certain embodiments, the metal component includes a metal foam having a porosity of from 0.89 to 0.97.

In certain embodiments, the metal component includes a metal foam having a thickness at least four times the skin depth of the metal.

In another aspect, this disclosure describes a method for cryoprotecting a biological tissue. Generally, the method includes contacting the biological tissue with any embodiment of the composition summarized above, freezing the tissue, and then rewarming the tissue.

In some embodiments, the tissue is rewarmed at a rate of at least 100° C./min.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 13. Properties of copper foams and aluminum foil. Heating rates are calculated from data from the first three seconds of heating.

DETAILED DESCRIPTION OF ILLUSTRATIVE EMBODIMENTS

Figure 1:
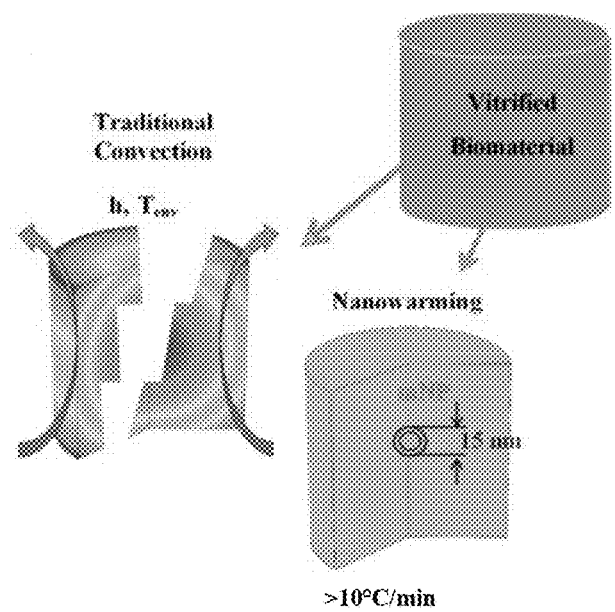
FIG. 1. Comparison of ultra-rapid metal foam/foil versus nanowarming (with nanoparticles) and standard convective warming. An order of magnitude higher heating is possible with foam/foil approach. (A) Schematic diagram of prior art nanowarming, and convective warming approaches. (B) RF heating of metal foam/foil for ultra-rapid warming. (C) Schematic diagram for ultra-rapid warming approach.
Figure 1:
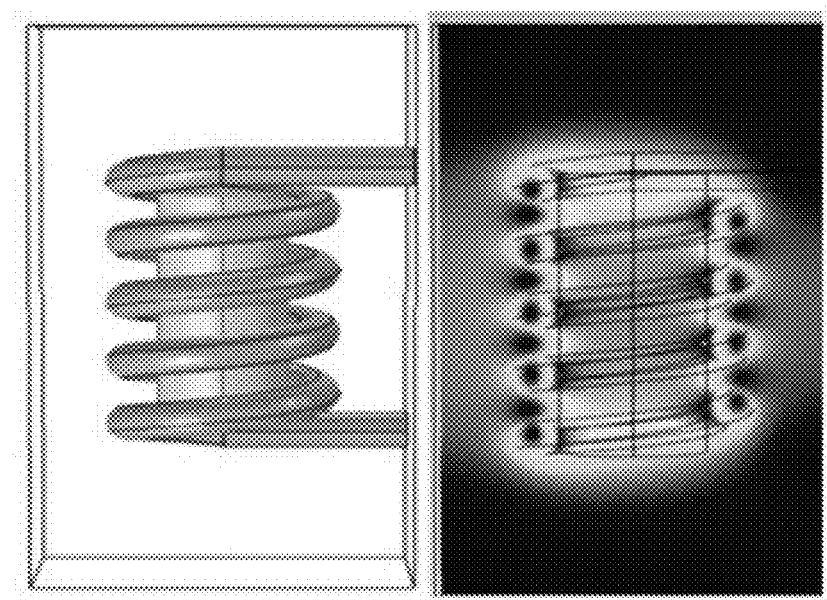
Figure 1:
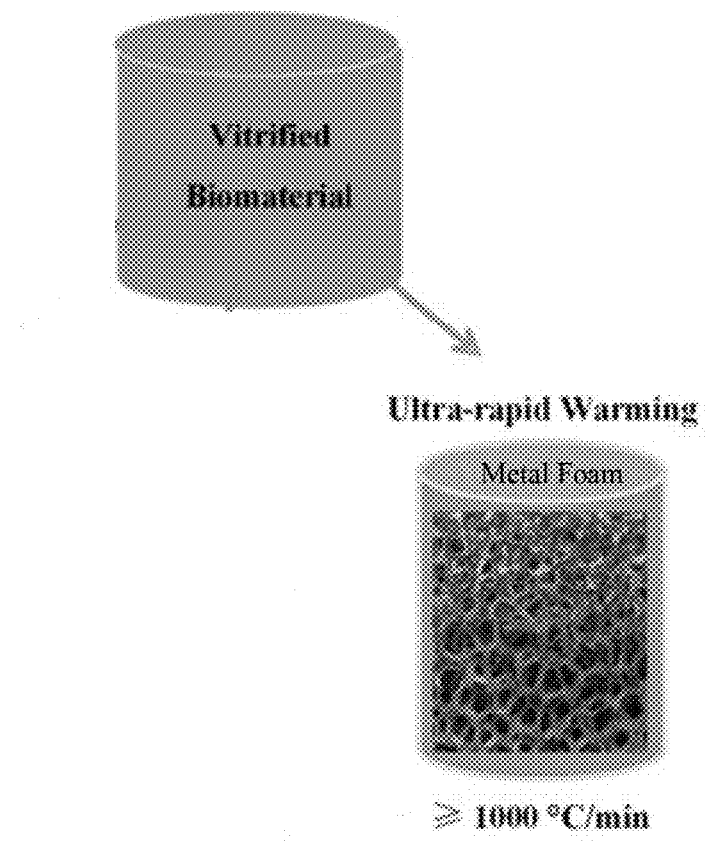
Figure 2:
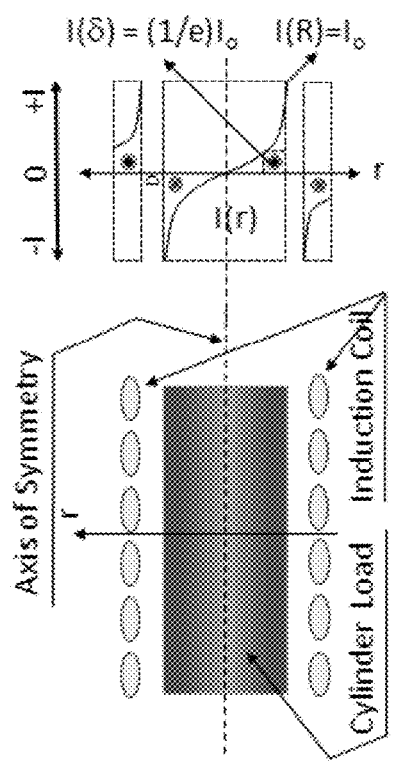
FIG. 2. Skin depth effect for design of metal foam, foil, or seeds for effective heating. (A) In an alternating electrical current (AC), I(r) does not distribute evenly within a conductor, and is largest near the surface of a conductor. (B) At a distance called the "skin depth," equal to one penetration depth below the surface ($\delta$), the current I(r) is seen to fall to 1/e (~0.37) of its surface value, $I_o$. The skin depth reduces with frequency increase.
Figure 2:
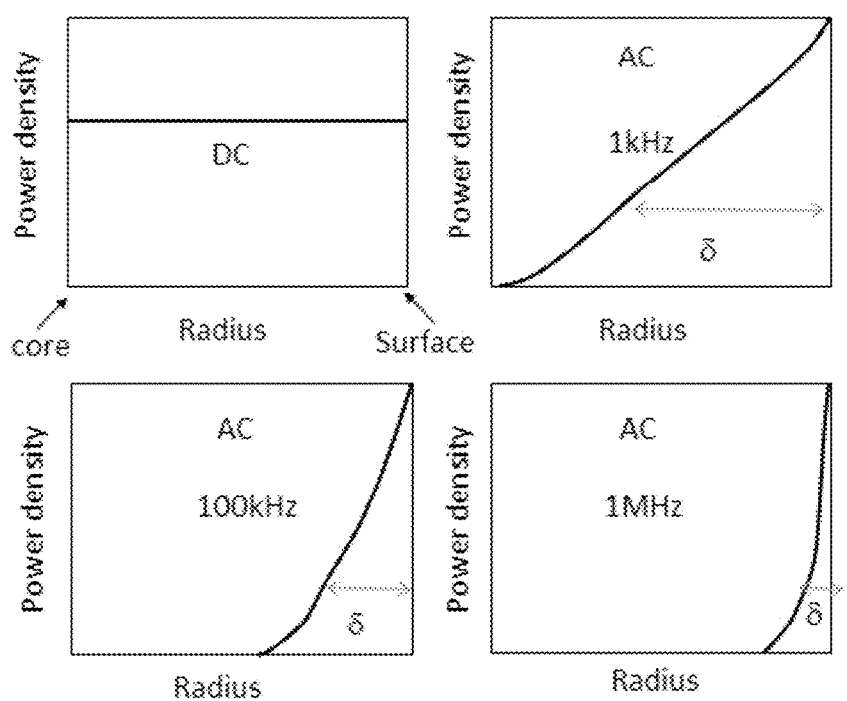

Vitrification is an attractive technology to bank and store tissues in a glassy versus crystalline state for eventual warming and use in regenerative medicine. For example, tissues have been successfully vitrified using high molarity (6-8.4 M) cryoprotective agents (CPA) such as VS55, DP6, and even glycerol, achieving critical cooling rates of 2.5° C./min, 40° C./min, and 85° C./min respectively. However, successful warming of bulk systems—i.e., cm size scales—from the vitrified state often cannot be achieved as it requires critical warming rates of 55° C./min, 185° C./min, and $3.2 \times 10^{4\circ}$ C./min for VS55, DP6, and glycerol, respectively (orders of magnitude higher than critical cooling rates) to avoid devitrification. Furthermore, these rates must be sufficiently uniform to avoid thermal stress that exceeds the yield stress (typically at least 2 MPa) thereby cracking the tissue. By achieving faster and yet uniform rates of cooling and warming the concentration of the cryoprotective agent can also be reduced thereby reducing chemical (i.e., cryoprotective agent) toxicity on the tissue during loading and unloading and potentially allowing vitrification and storage of more tissues to become a standard practice.

This disclosure provides a new technology based on inductive heating of metal foams, metal foils, and/or metal seeds. A model metal foam of copper and a model metal foil of aluminum were tested. The copper foam and aluminum foil exhibit high electrical conductivity. While described below in the context of exemplary embodiments using the copper foam or aluminum foil, the compositions and methods described herein can involve—or can involve the use of—a metal foam, a metal foil, or a metal seed that includes other metals. Exemplary embodiments can include, for example, a foam of copper or other ferromagnetic material such as, for example, cobalt, iron, iron oxide, nickel-iron oxide, copper-iron oxide, magnesium-iron oxide, nickel, manganese antimony, manganese iron oxide, yttrium iron oxide, chromium oxide, manganese arsenic, gadolinium, terbium, dysprosium, europium oxide. Additional exemplary materials include diamagnetic materials such as, for example, a superconductor, pyrolytic carbon, bismuth, silver, carbon (diamond), lead, carbon (graphite), copper, and/or their alloys.

A metal foil can include aluminum, copper, iron, or any of the materials listed above as suitable for use in a metal foam. Similarly, a metal seed can include copper, aluminum, iron, or any of the materials listed above as suitable for use in a metal foam.

The cryoprotective composition—whether a metal foam, metal foil, or metal seed—generally can be prepared by combining a cryoprotective agent with a metal foam, metal foil, or metal seed. In one exemplary embodiment, VS55 (Fahy et al., 1984, *Cryobiology* 21(4):407-426; Mehl, P. M., 1993, *Cryobiology* 30(5):509-518) is used as the cryoprotective agent. Alternative exemplary cryoprotectant agents that may be used to prepare a metal foam, foil, or seed system are listed in Table 1.

TABLE 1

Properties of exemplary cryoprotective agents.

| | 6M glycerol | VS55 | DP6 | M22 |
|---|---|---|---|---|
| Melt Temperature ($T_m$) | −26° C. | −38° C. | −34° C. | −54.9° C. |
| Glass Transition Temperature ($T_g$) | ~−100° C. | −123° C. | −119° C. | ~−120° C. |
| Critical Cooling Rate | −85° C./min | −2.5° C./min | −40° C./min | 0.1° C./min |
| Critical Warming Rate | $3.2 \times 10^4$ C./min | 50° C./min | 185° C./min | <1° C./min |

Similarly, alternative metals or materials may be used to produce a cryoprotectant metal foam, so long as the metal has a sufficiently high Curie temperature. For example, metals with variable skin depths that can be used to produce foams, foils, or seeds are listed in TABLE 2 along with specific examples of skin depths with which the foam, foil, or seed may be used.

TABLE 2

Penetration depth of metals in μm

| Metal | μ μH/m | ρ μΩ·m | Frequency (kHz) | | | | |
|---|---|---|---|---|---|---|---|
| | | | 1 | 5 | 30 | 100 | 360 | 480 |
| Copper | 1.256 | 0.0017 | 2063 | 923 | 377 | 206 | 109 | 94 |
| Aluminum | 1.256 | 0.0026 | 2591 | 1159 | 473 | 259 | 136 | 118 |
| Iron | 6300 | .0097 | 70 | 31 | 12.8 | 7 | 3.7 | 3.2 |
| Workpiece type: | | | | | Thick workpiece | | Small workpiece | Microscopic |

In one exemplary embodiment, the metal foam component of the composition included a copper metal foam having 20 pores per inch (20 PPI), a porosity of 0.94, and a density of 0.49 g/cm³ (FIG. 13) and was deployed directly into a 1 mL cryovial filled with VS55 (8.4 M) as a cryoprotective agent. Additional exemplary copper metal foams are shown in the first three lines of FIG. 13. An exemplary aluminum foil is shown in the final line of FIG. 13.

Figure 3A:
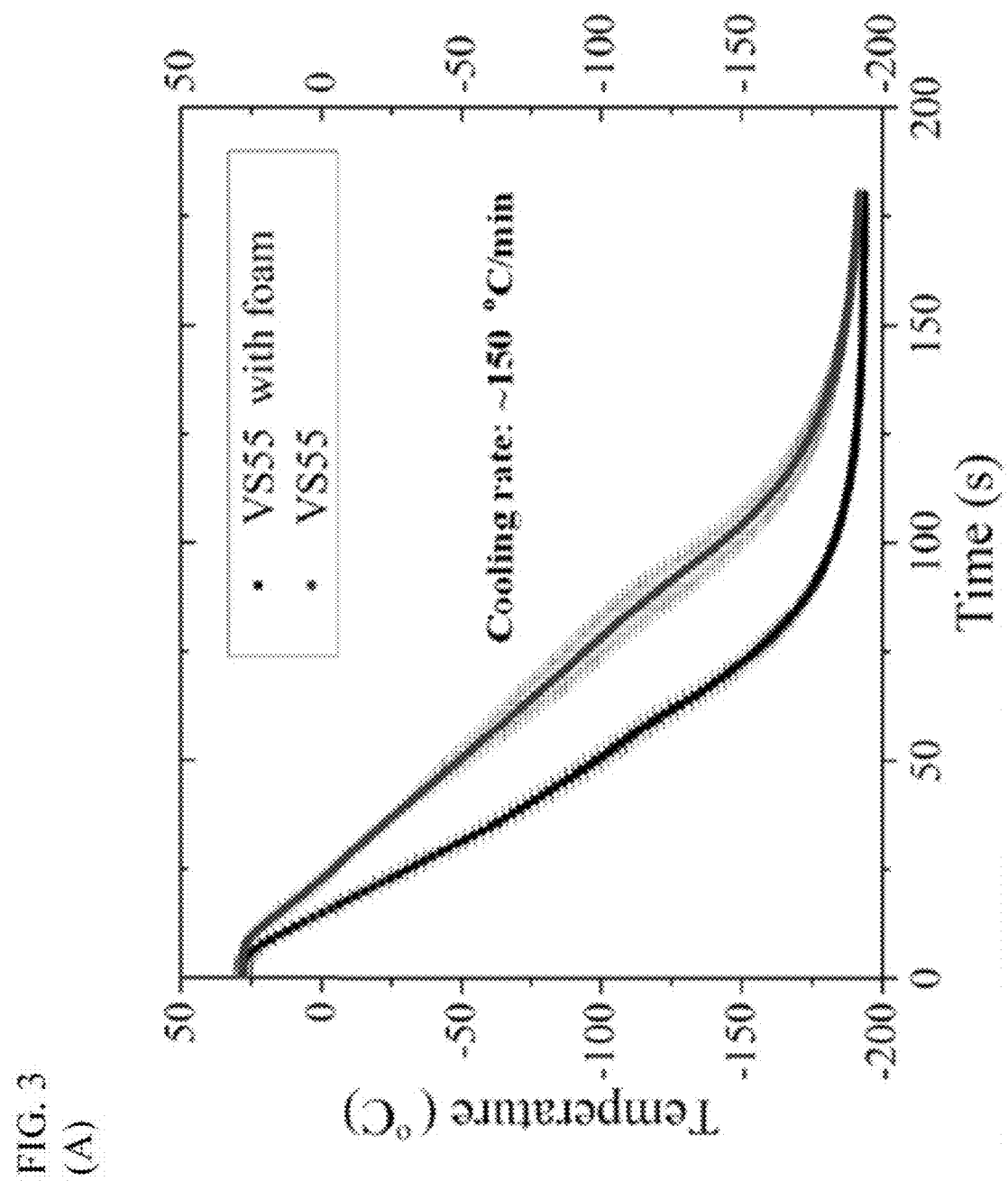
FIG. 3. Fast cooling of biomaterials with metal foams. (A) Thermal response (Cooling rate of 150° C./min) in VS55 with metal foam exceeds that in VS55 without foam present after immersing the sample in liquid $N_2$. (B) Schematic of experimental set up for immersion cooling with metal foam (0.94-20 PPI).
Figure 3:
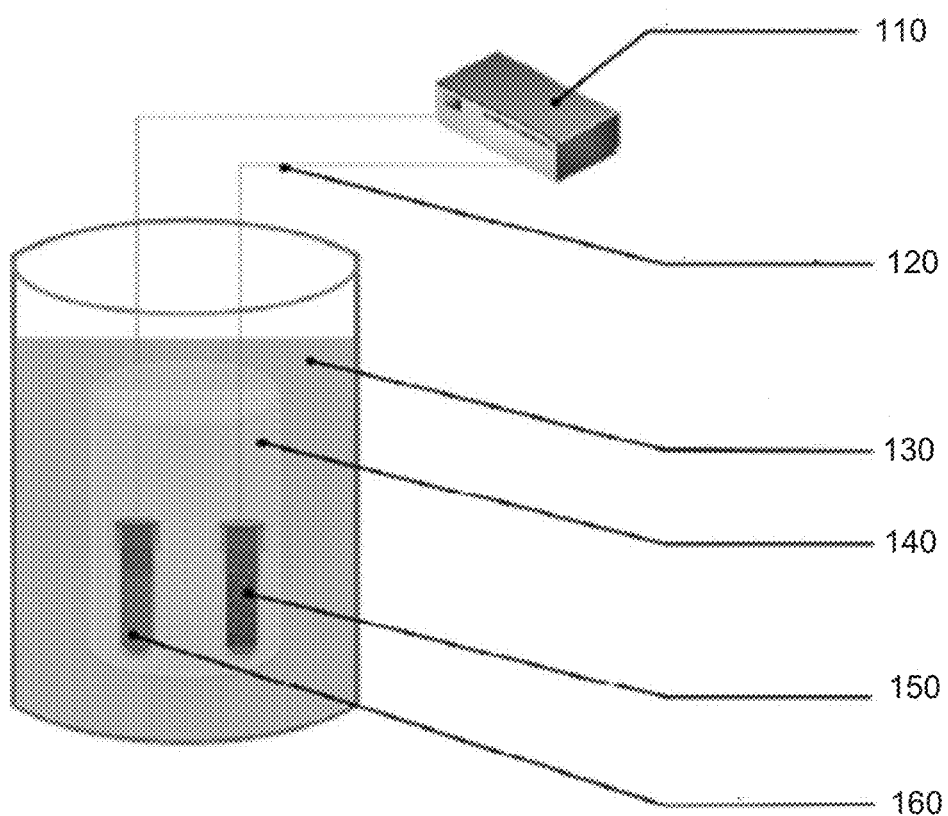
Figure 4:
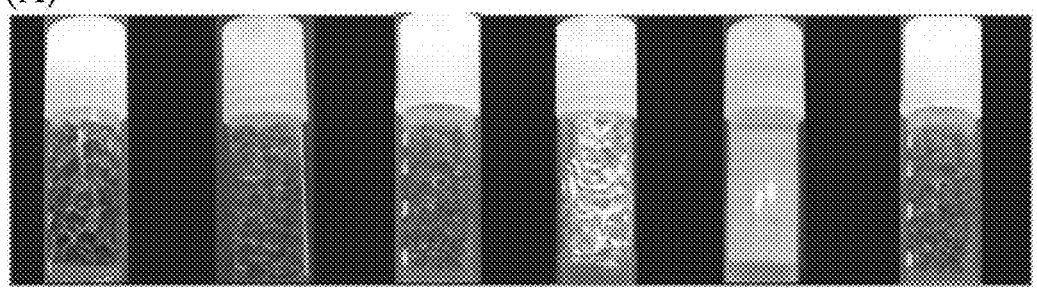
FIG. 4. Controlled cooling with metal foams and foils. (A) Loading of VS55 in a 1.8 mL cryovial containing copper foam or aluminum foil at 20° C. (B) Success and failure of cooling same vials to sub-glass transition temperature of approximately −140° C. (C) Warming methods: vitrified samples are rewarmed by two methods, either convectively (i, left) or through RF heating (ii, right).
Figure 4:
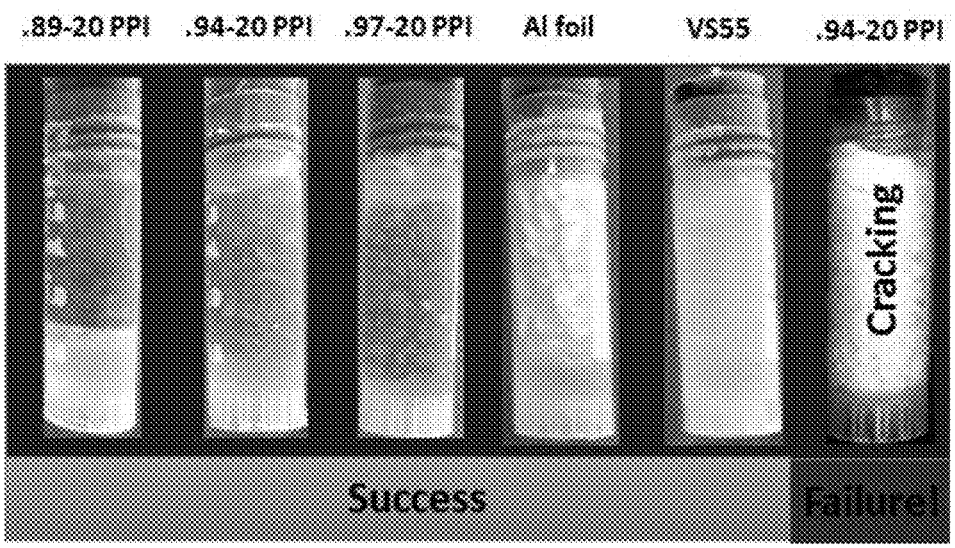
Figure 4:
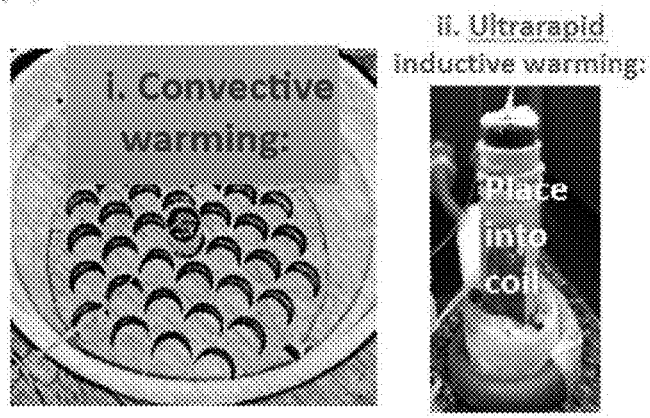
Figure 5:
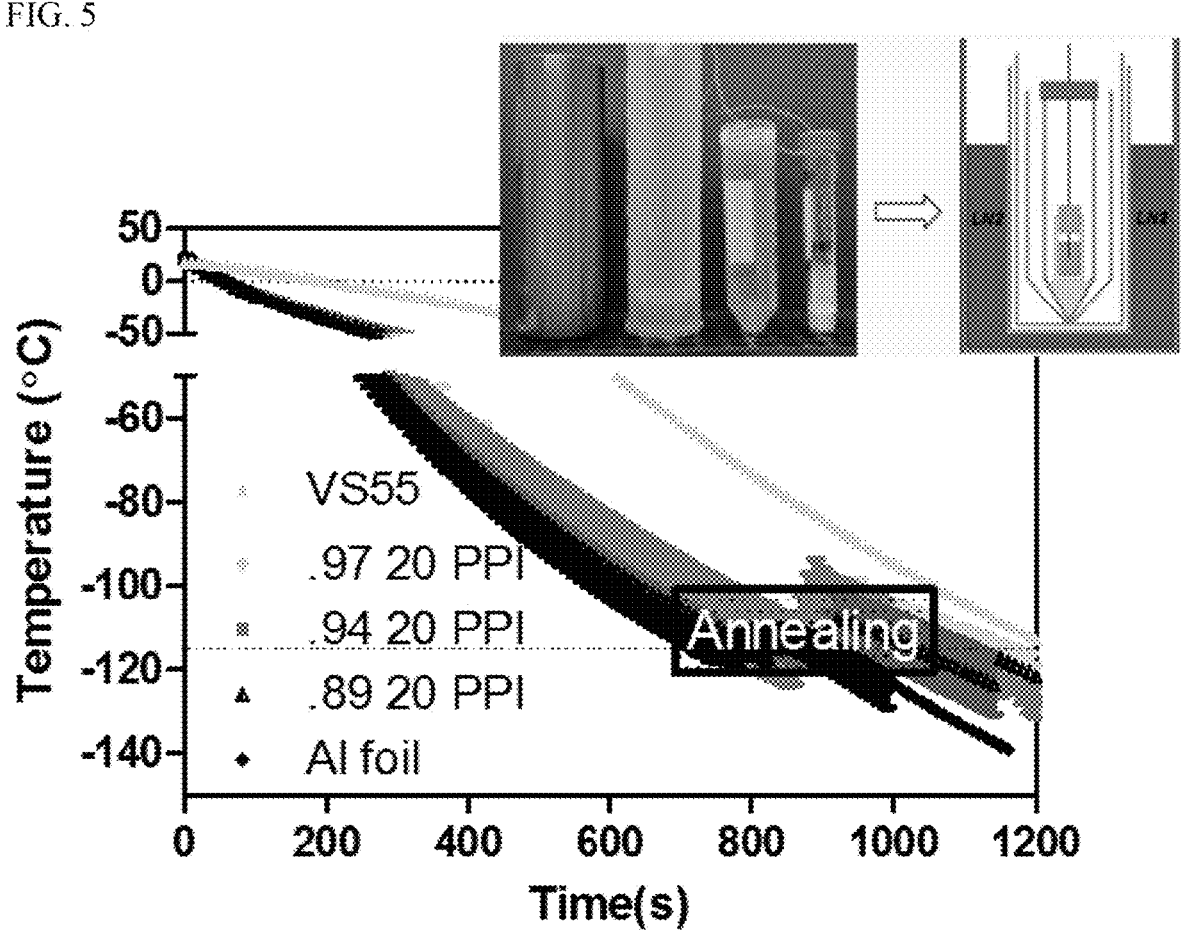
FIG. 5. Slow controlled cooling profile using a multiflask approach for a sample containing VS55, foam, or foil with VS55 (8-10° C./min). The presence of metal in VS55 enhances the cooling. The cooling technique is the same as reported in (Etheridge et al., 2014, *Technology* 2(03):229-242).
Figure 6:
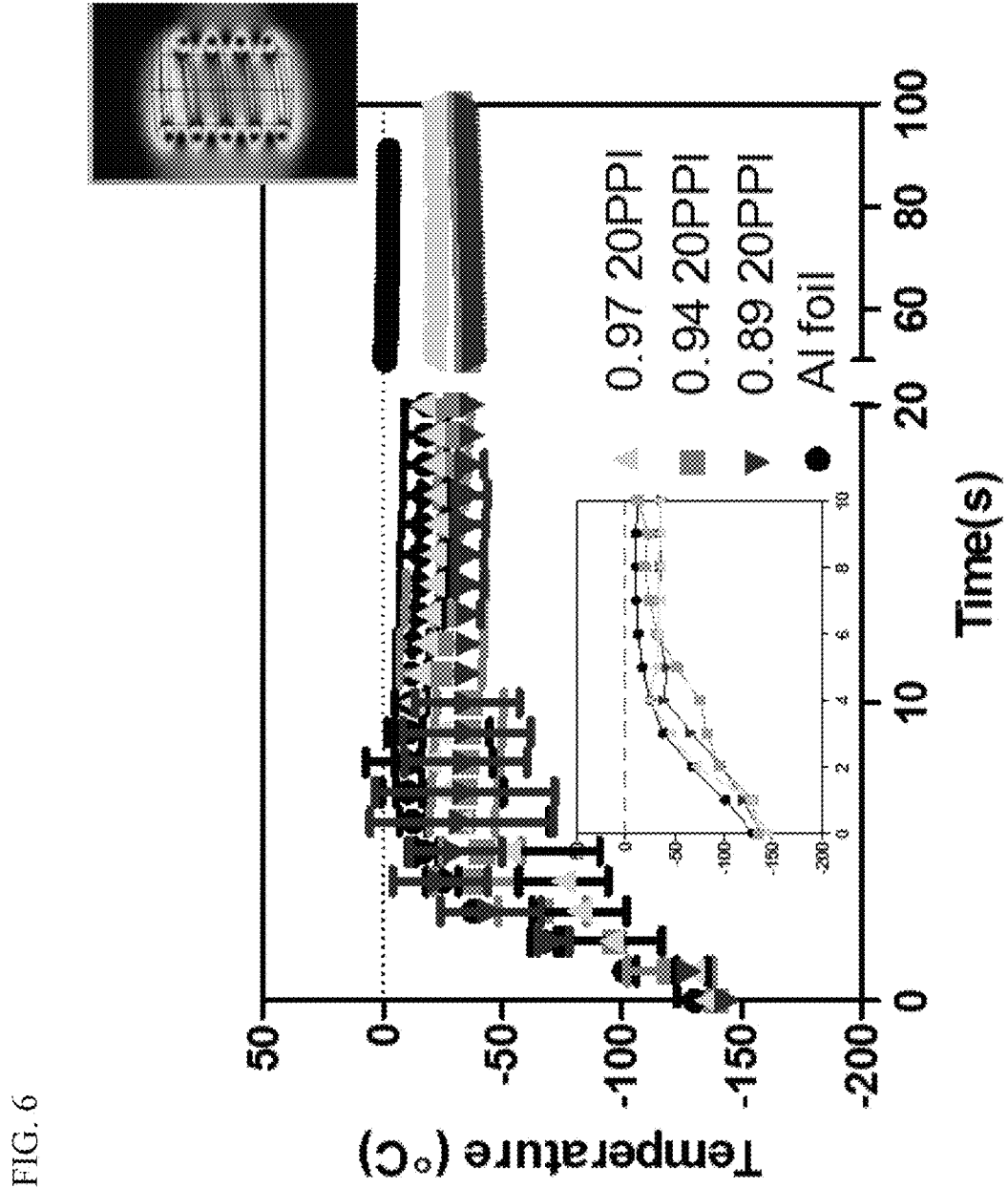
FIG. 6. Ultra-rapid warming profiles using 20 PPI (pores per inch) of copper foams with different porosities (89%, 95%, or 97%) and aluminum foil in an initially vitrified VS55 solution with ultra-rapid rates (~1000-2000° C./min). Here, Specific Absorption Rate (SAR) ~100-300 W/cm$^3$ were experimentally measured in the copper foams or aluminum foil system exposed to RF (20 kA/m and 360 kHz).
Figure 7:
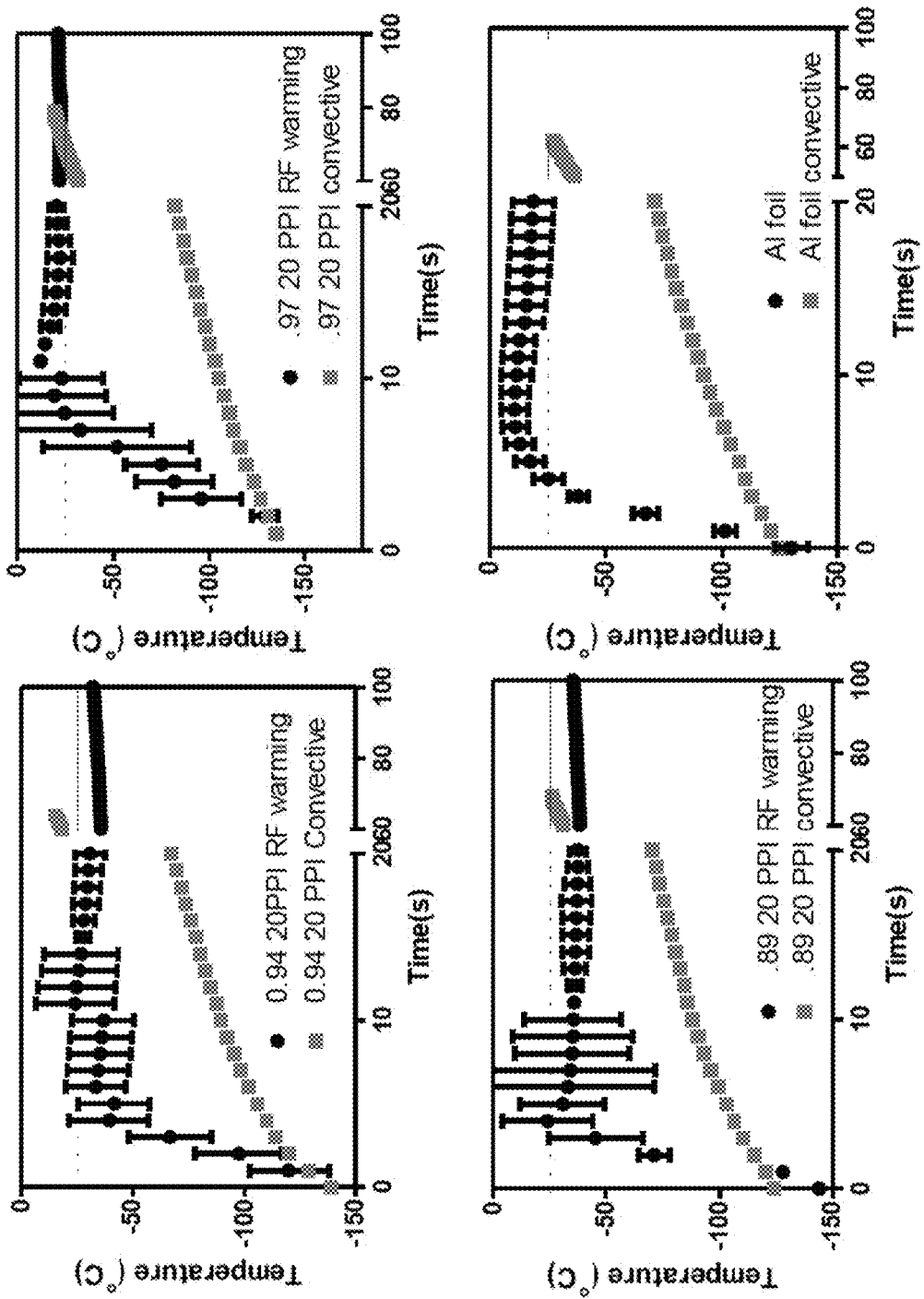
FIG. 7. Heating profiles of vitrified samples containing several copper foams and aluminum foil in VS55 exposed to RF (20 kA/m and 360 kHz) or rewarmed convectively in water bath (20° C.). The melt temperature for VS55 is −32° C. and therefore warming is intentionally stopped before going above 0° C.
Figure 8:
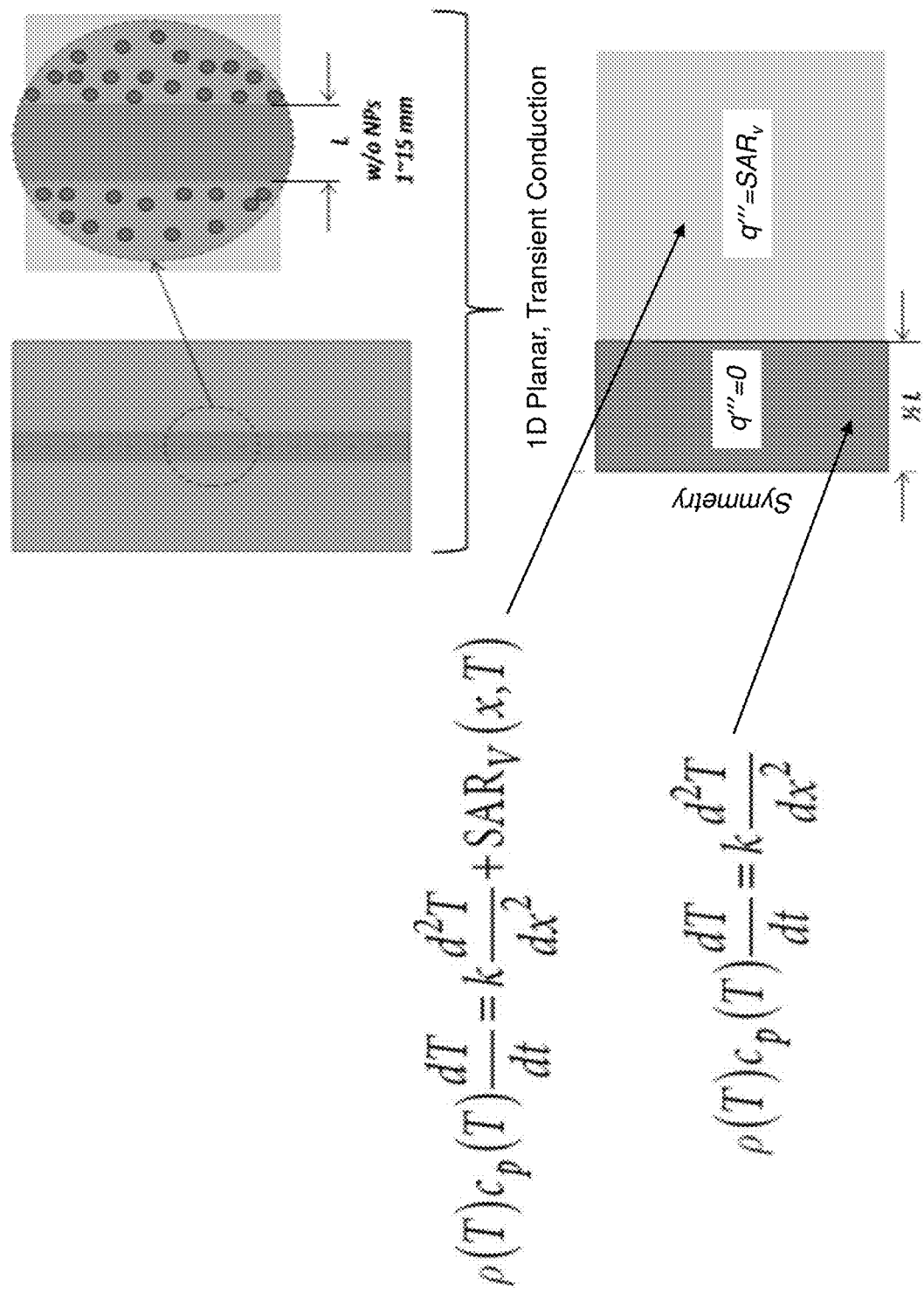
FIG. 8. Computational modeling simulation for a generally planar tissue.
Figure 9:
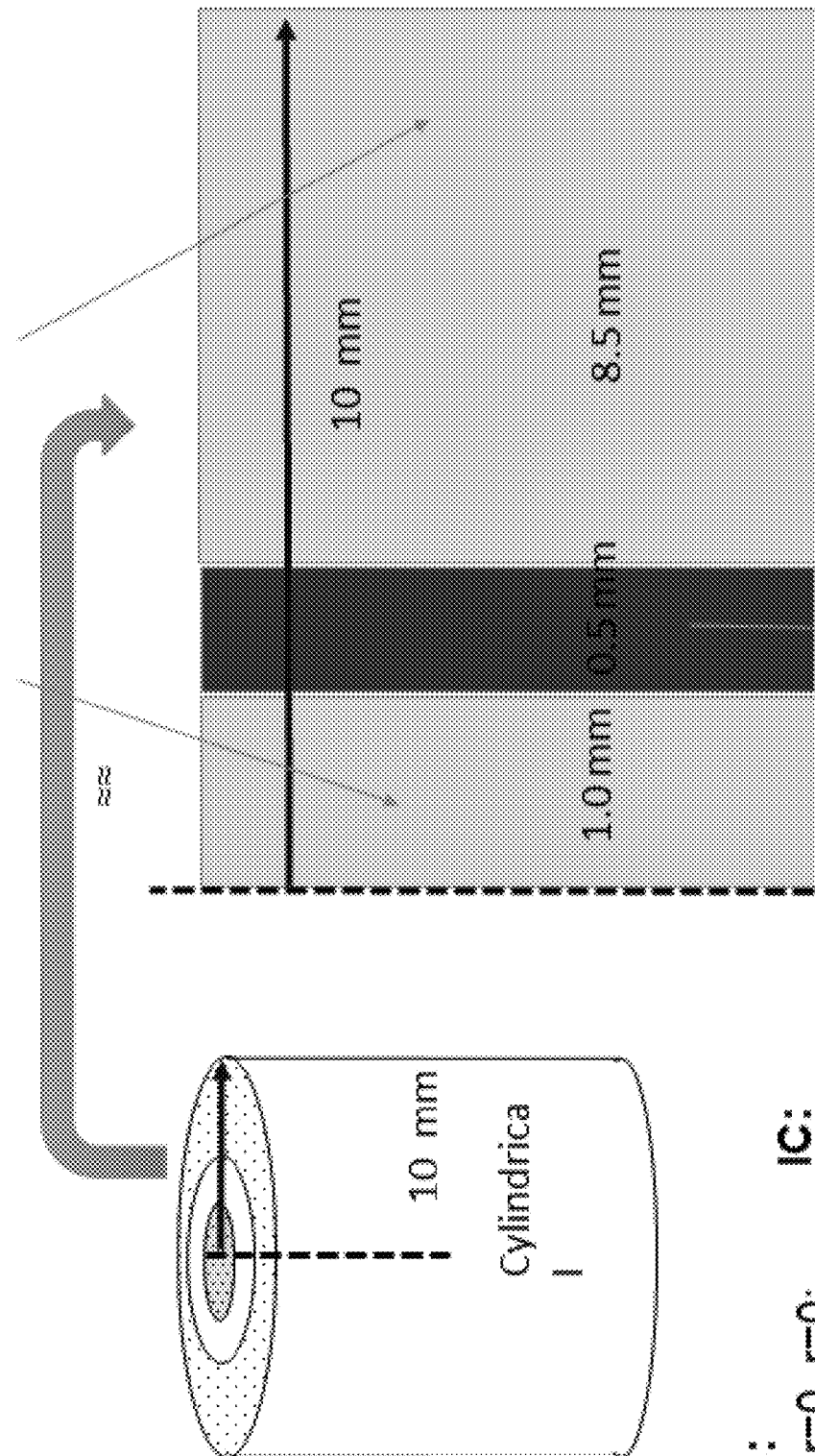
FIG. 9. Computational modeling simulation for a generally cylindrical tissue.
Figure 10:
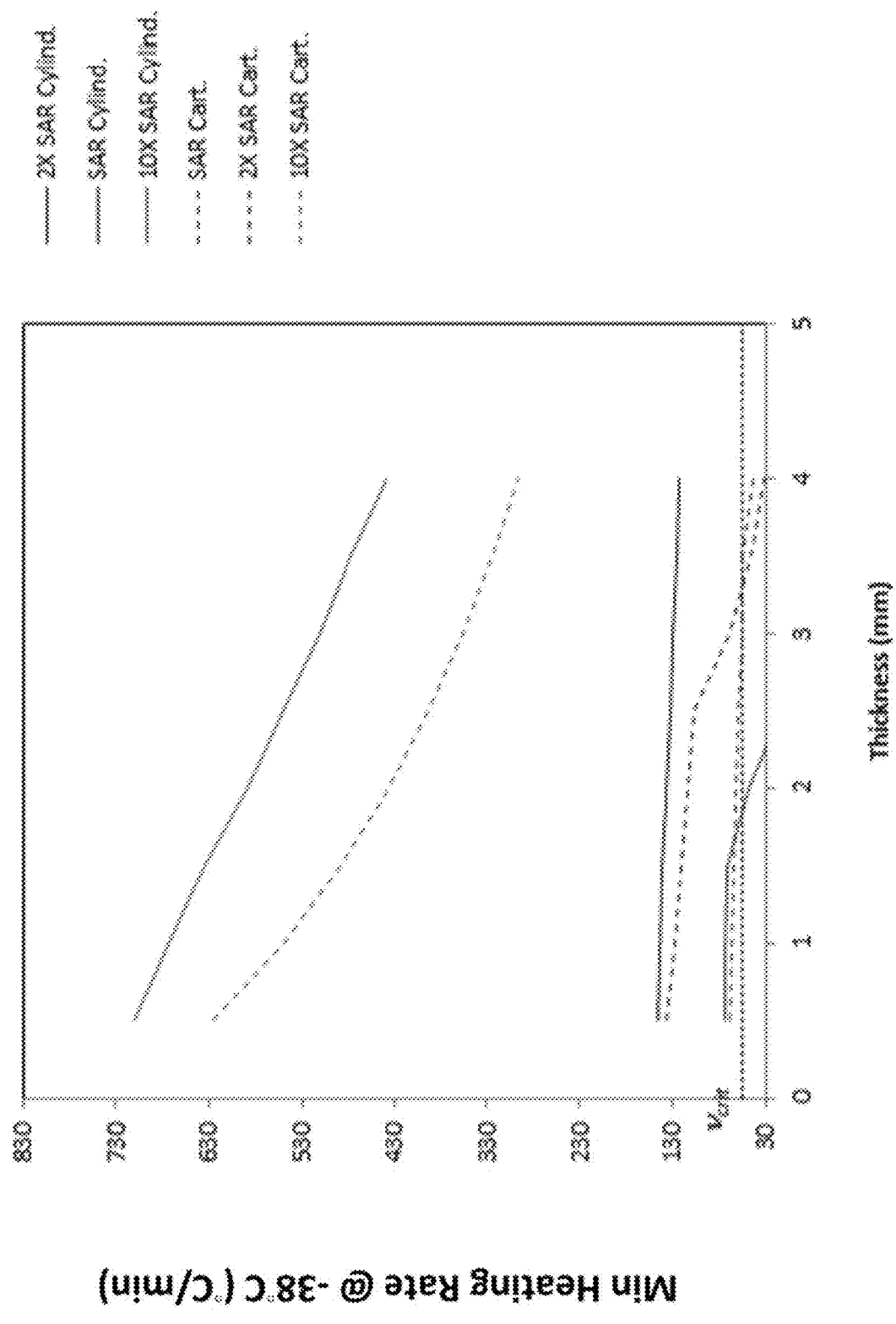
FIG. 10. Simulation minimum heating rates. Comparison of simulation heating rates for planar (Cartesian) versus cylindrical (Cylindrical) tissues as a function of tissue thickness.
Figure 11:
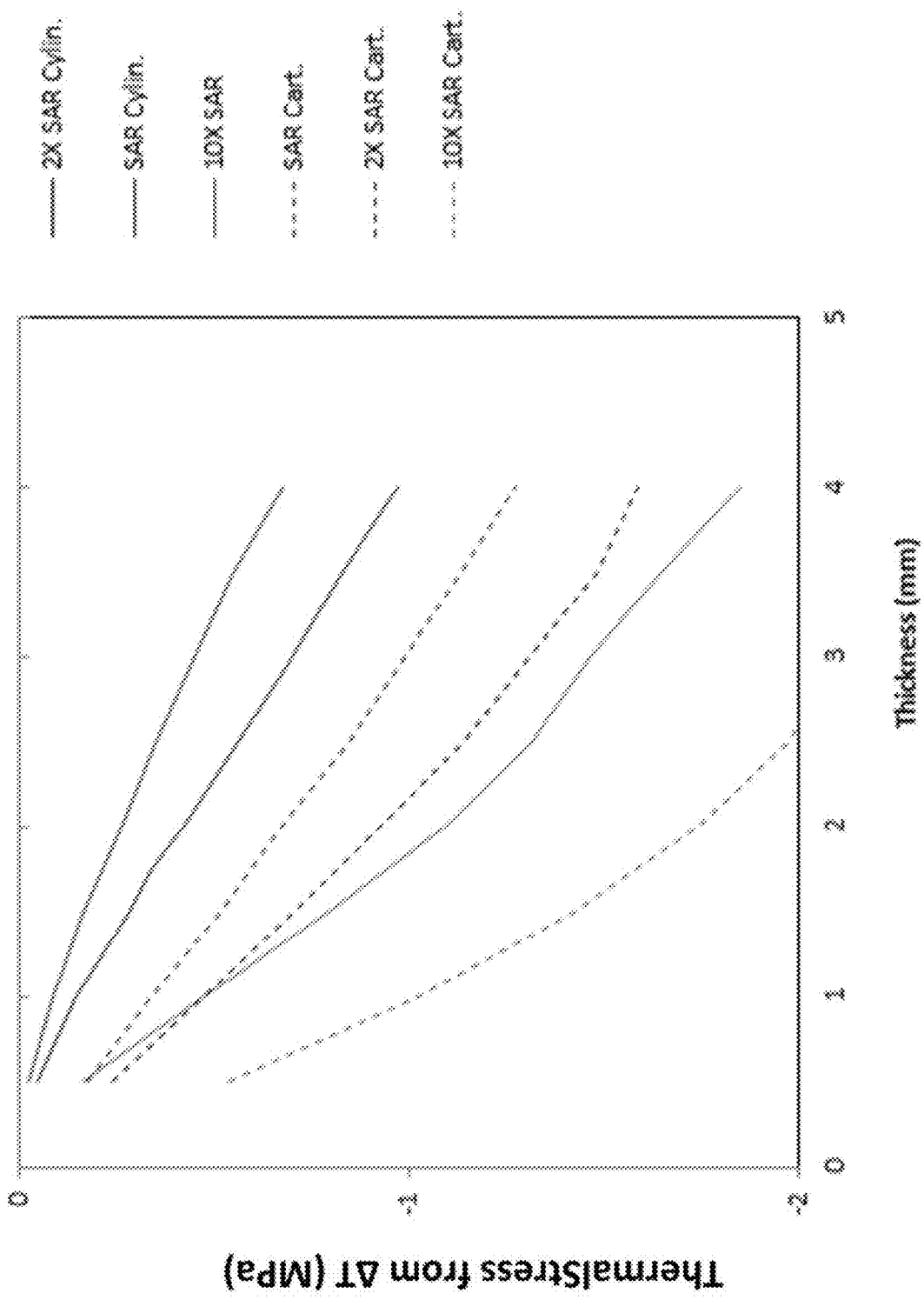
FIG. 11. Simulation thermal stress. Comparison of thermal stress for planar (Cartesian) versus cylindrical (Cylindrical) tissues as a function of tissue thickness.
Figure 12:
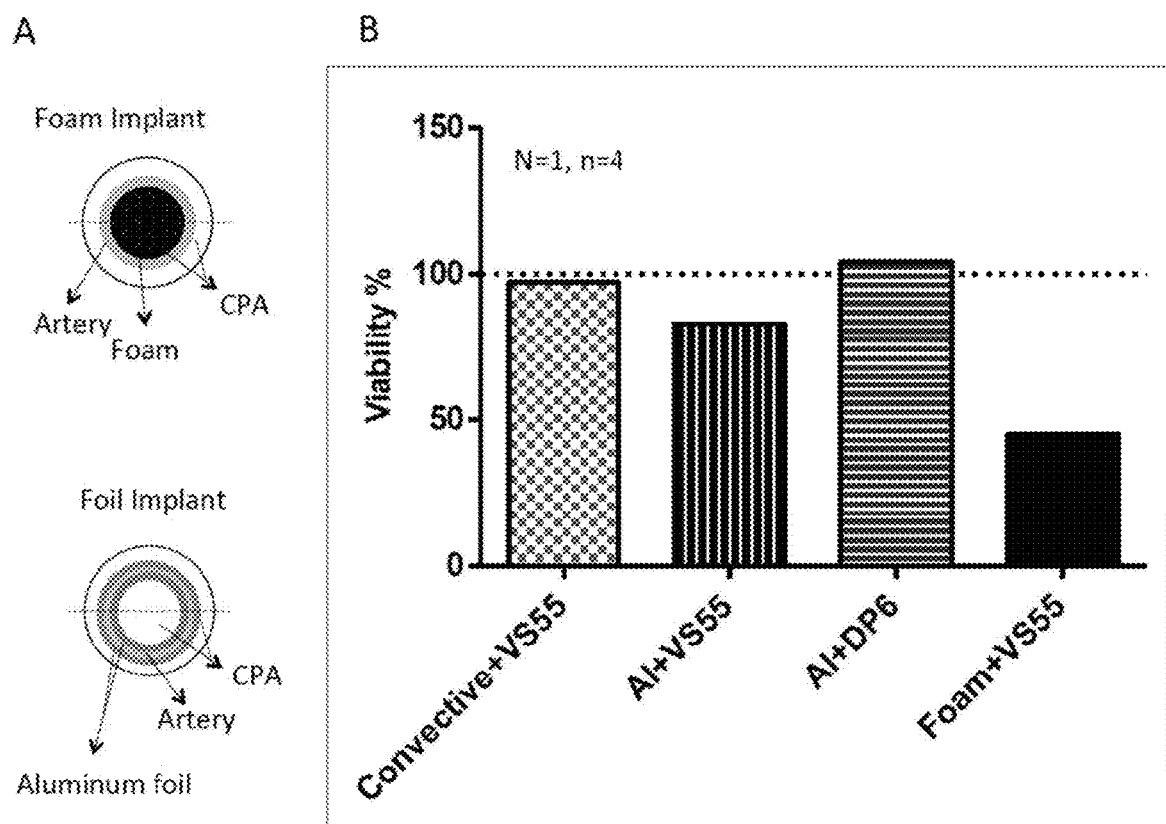
FIG. 12. Example biological data from ultra-fast warming. (A) Schematic showing implantation of copper foam and aluminum foil in carotid arteries for ultra-rapid rewarming. (B) The ALAMARBLUE® cell viability assay (Thermo Fisher Scientific, Inc., Waltham, Mass.) results showing the highest viability response from aluminum foil in DP6 (6 M CPA) versus foil or metal foam in higher concentration CPA (VS55). This data is based on number of experiment (n) and number of segment tested (N) to be n=1, and N=4.

Controlled cooling to the vitrified state at rates between 10° C./min to 100° C./min was achieved by exposure to liquid-nitrogen-cooled gas or liquid environments (FIG. 3, FIG. 4, and FIG. 5). FIG. 6 shows controlled warming rates up to 2000° C./min and specific absorption rate (SAR) of up to 233 W/cm³ were experimentally measured in systems using copper foam or aluminum foil exposed to radio frequency (RF) current (20 kA/m and 360 kHz). This compares to SAR of only 1-10 W/cm³ in many nanowarming (iron oxide nanoparticle) embodiments. Computational modeling suggests that tissues up to several mm thick can be warmed by this technology at rates up to 2000° C./min without cracking (i.e., thermal stress <yield stress). Thus, the methods described herein can be practiced on planar or cylindrical tissues of mm scale thickness such as skin, cartilage, heart valves, small vessels (arteries and veins), and reproductive tissues (i.e., ovaries and testes). For instance, copper foams and aluminum foils were designed to fit within—or around in the case of foil—a carotid artery segment with DP6 (6 M CPA) and VS55 (8.4 M CPA). FIG. 12 shows viability using an exemplary metal foil with low concentration CPA (Al+DP6) greater than when using either foam with VS55 (Foam+VS55) or foil with VS55 (Al+VS55). This demonstrates the potential for higher heating rates to work with lower concentrations of cryoprotectant agents, thereby reducing toxicity.

While described in detail herein in the context of an exemplary embodiment, alternative metal foams, metal foils, or metal seeds, alternative RF fields, alternative cryoprotective agents, alternative cryoprotectant concentrations, and alternative tissues are possible.

Conventional "nanowarming" methods (e.g., those described in (Etheridge et al., 2014, *Technology* 2(03):229-242) are carried out with commercially available magnetic nanoparticles at 10 mgFe/mL (~15 mg metal oxide/mL). This approach is capable of inducing specific absorption rate (SAR) around 1.6-2.5 W/cm³. In contrast, warming methods that use a metal foam, a metal foil, or a metal seed can achieve up to 370 W/g in copper foam geometry and 416

W/g in aluminum foil geometry with cryoprotective solutions. These metal foams and metal foils can generate 89-233 W/cm$^3$ SAR. Thus, both the SAR and the corresponding rewarming rate, which is directly proportional to SAR, can be improved by at least two orders of magnitude—i.e., from 100° C./min using conventional "nanowarming" methods to 1,000° C./min or even 10,000° C./min by using a metal foam, metal foil, or metal seed. By heating at such high rates, one can reduce the concentrations of the cryoprotective agent and thus reduce the toxicity associated with these chemicals.

Thus, in certain embodiments, the method can involve rewarming the tissue at a minimum rate of at least 100° C./min such as, for example, at least 500° C./min, at least 600° C./min, at least 700° C./min, at least 800° C./min, at least 900° C./min, at least 1000° C./min, at least 1200° C./min, at least 1400° C./min, at least 1600° C./min, at least 1800° C./min, at least 2000° C./min, at least 2500° C./min, or at least 5000° C./min. In one embodiment, the method involves rewarming the tissue at a rate of at least 1000° C./min. In another embodiment, the method involves rewarming the tissue at a rate of 10,000° C./min.

In addition, rewarming tissues using a metal foam, metal foil, or metal seed can allow one to completely avoid the use of magnetic nanoparticles, any concerns with their use in the cryoprotective agent, and/or their removal from the tissue after rewarming. While each tissue (e.g., artery, skin, cartilage, heart valve etc.) is expected to present with several sizes and shapes, one can easily select and/or modify a metal foam to fit the tissue. For instance, one can tailor foams, foils, or seeds to fit different sizes (i.e., S, M and L and/or curved) for each potential tissue type. The metal foam will be simply removed from the lumen or surface of the tissue after use and the tissue can be further unloaded of cryoprotective agent and/or used directly. The foil is particularly easy to shape to fit numerous geometries at the time of deployment in a tissue.

Warming rates and, therefore, foam or foil conditions may vary depending on the cryoprotective agent used. Thus, the method can involve tailoring conditions for a given tissue, cryoprotective agent, and foam or foil in a specific inductive and resistive heating field in order to achieve the least cryoprotective agent toxicity and the maximum viability outcome post vitrification.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cryoprotectant Solutions

DP6 is a cocktail of 234.4 g/l DMSO (3M), 228.3 g/l propylene glycol (3M), and 2.4 g/l HEPES in EuroCollins solution (Fahy et al., 1984, *Cryobiology* 21(4):407-426; Mehl, P. M., 1993, *Cryobiology* 30(5):509-518). VS55 is a cocktail of 242.14 g/l DMSO (3.1M), 168.38 g/l propylene glycol (2.2M), 139.56 g/l formamide (3.1M), and 2.4 g/l HEPES in EuroCollins solution.

A 5× Euro-Collins stock solution was prepared starting with 0.5 L of water, to which the following components were added in order with stirring: 174.76 g dextrose, 10.2 g KH$_2$PO$_4$, 36.5 g K$_2$HPO$_4$, 5.6 g KCl, and 4.2 g NaHCO$_3$. Additional water was added to bring the total volume up to 1 L, then filtered.

Fresh cryoprotectant solutions were prepared for each day of experiments

Metal Foam and Cryovials

Physical Study

The metal copper foams 150 (Pores per inch (PPI): 20, porosity: 0.89, 0.94, and 0.97) were cut into cylinder shape, which had the diameter of 9.8 mm and height of 23 mm. To avoid the thermocouple 120 contact with the metal foam 150, a 1 mm hole was drilled in the center axis of metal foam/foil. The metal foams were put into 2 mL cryovials (NUNC, Thermo Fisher Scientific, Waltham, Mass.) while the CPA was added later to fill the voids until reaching the 1.8 mL line of cryovials. One 1 mm hole was drilled in the center cryovials lid for putting the thermocouple in, and the thermocouples were located in the center axis of cryovials, while the vertical position was 30 mm from the top of cryovials with the lid of cryovials).

Viability Study

For the rewarming of vitrified carotid artery using foam metal seed, the foam is trimmed to fit the artery inner diameter while the outside was exposed only to CPA. The foil heating has been pre-formed by wrapping aluminum foil from inner and outer side of the carotid segments (sandwich) and the rest area was filled with the CPA.

Cooling Approaches

Direct Cooling

For direct cooling in liquid nitrogen 130, a 50 mm diameter of cylinder shaped container 140 was used. The cryovials 160 were directly immersed into container 140. The whole liquid nitrogen container transferred into the liquid nitrogen bottle (−196° C.). A temperature recorder 110 (LR8431, Hioki USA Corp., Cranbury, N.J.) and thermocouples 120 (T type, Omega Engineering, Inc., Norwalk, Conn.) were used to measure the temperature variation, which started to monitor the temperature when cryovials were placed into liquid nitrogen container.

Controlled Cooling

To achieve controlled cooling rates, the multi-flask cooling, technology for 1 mL system was utilized as described in detail in our previous studies (Etheridge et al., 2014. *Technology* 2:229-242). The cryovials were first placed in a series of containers thus the system has several plastic and air barriers. This has two major benefits as this approach decreases the effective convective heat coefficient of liquid nitrogen and also lowers the chance of contamination during viability assessments. The temperature was monitored by thermocouples during cooling process. To lower the chance of cracking due to the dramatic viscosity changes around glass transition, annealing was applied (few seconds) around −115° C. just before reaching the glass transition temperature (−123° C.) of VS55. Then the frost on cryovials were wiped, and returned to the cooling container. The annealing process helps the inner structure to balance with the outer boundary temperature and release some of the accumulated thermal stresses. Then the samples were held at sub-glass-transition-temperature, approximately −140° C., monitored for any crack and if successfully vitrified then placed either in RF system or convective water bath for rewarming process.

Warming Approaches
Convective Warming

The vitrified samples were transferred from liquid nitrogen container and immersed into 37° C. water bath while the temperature variation was recorded using prepositioned fine T type thermocouples (40-gauge) in the middle of sample. The experiments were suspended at −20° C. above the melting temperature of DP6 (−34° C.) and VS55 (−38° C.) to lower the toxicity effect of CPA at high temperatures for viability assessments.

RF Warming

VS55 solutions with and without foam were heated in 1 kW Hotshot inductive heating systems with 2.5-turn, water-cooled copper coil (Ameritherm Inc., Scottsville, N.Y.) with magnetic field at 10-25 kA/m (peak, volume-averaged field strength) and 190-360 kHz. The cryoprotectant solutions were cooled down using a multiflask controlled approach (Etheridge et al., 2014, *Technology* 2(03):229-242) to below the glass transition temperature (Tg: −123° C. for VS 55) ~−140° C., at sufficient rates to produce vitrification and then quickly transferred into the inductive coil for immediate heating inside a sealed styrofoam, to lessen direct losses to the environment. Fine thermocouples (40-gauge) were embedded in the middle of sample prior to cooling and provided continuous temperature monitoring in conjunction with a Fluke 52 digital thermometer system (Fluke Inc., Plymouth, Minn.). RF fields are expected to produce interference in metallic thermocouples, but this was characterized and found to be negligible (around 0.2° C. to 0.3° C.) in the ultrafine gauge thermocouples used (Etheridge et al., 2014, *Technology* 2(03):229-242). The sample temperature data from the control and RF heated samples were used to calculate the heating rate and estimate the SAR generated from foam/foil. The sample temperature was acquired at a frequency of 1 Hz, so the heating rate was calculated from the temperature difference between each measurement point, divided by the elapsed time; and the temperature was then taken as the average between those two points.

RF Field Characterization

To characterize the RF field, the radiofrequency module in the COMSOL software (Comsol, Inc., Burlington, Mass.) was used to simulate the magnetic field in the RF coil based on the applied alternative current. The coil has 2.5 turns having geometric parameters mimicking the RF system being used in experiments. The material of coil was set as copper and the other spaces were set as air. The electric current in the coil was set as 280 A. The model was developed to understand the extent of the homogenous magnetic field or volume of interest (VOI). The fields were verified by direct measurement with a commercial 2D magnetic field probe (Fluxtrol) at the center of the coil for 360 kHz at different power levels.

Viability Assessment

Porcine arteries were removed half an hour after death, placed in growth media and carried out on ice to lab. Upon receipt, arteries were dissected to reproducible segments of approximately 1 cm in height. The viability of rewarmed arteries by ultra-rapid rewarming or fast convective warming were assessed by ALAMARBLUE® cell viability assay (Thermo Fisher Scientific, Inc., Waltham, Mass.). The artery vessels were incubated with 10% ALAMARBLUE® cell viability assay (Thermo Fisher Scientific, Inc., Waltham, Mass.) media solution at 37° C. for three hours before any rewarming experiments. Fluorescence was read on a plate reader (Synergy HT, BioTek Instruments, Inc., Winooski, Vt.) at 590 nm from an aliquot of the media to establish a baseline. The tissues were loaded with CPA in a stepwise manner. All samples were successfully vitrified and transferred to rewarming apparatus when they reached −140° C. Then samples were then rewarmed either by RF coil (20 kA/m, 360 kHz) or by convective rewarming (gold standard for samples <3 mL) using 37° C. water bath immersion. After the removal of the CPA, the tissue segments were sectioned into small pieces and incubated with fresh media at 37° C. for one hour (recovery procedure) and then incubated with 10% ALAMARBLUE® cell viability assay for three hours. The viability of each tissue piece was calculated by comparing the fluorescence readings before and after cooling and rewarming and normalized to fresh control. All the results are presented as the mean±standard error of relative fluorescence units (RFU) after correction to RFU/mg dry weight results as a percent of control.

Example 2

Commercial household aluminum foil was rolled into hollow cylinder shape having the same diameter and height as the foam cylinder and the rest volume was loaded with VS55 to reach 1.8 mL. The physical study of the performance of the aluminum foil was performed as described in EXAMPLE 1.

For biological study, the aluminum foil was cut and shaped to fit the inside and outside surface of the artery segments. All other details are the same as given in EXAMPLE 1.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
    contacting a biological tissue with a composition comprising:
        a cryoprotective agent; and
        a metal component comprising a metal foam, a metal foil, or a metal seed;
    cooling the tissue; and
    rewarming the tissue, wherein the rewarming comprises inductive heating of the metal component by placing the metal component and the tissue within an electromagnetic induction field.

2. The method of claim 1 wherein the rewarming of the tissue is at a rate of at least 100° C./min.

3. The method of claim 1, wherein
    the metal component comprises copper, aluminum, iron, or a combination thereof.

4. The method of claim 1, wherein the metal component comprises an aluminum foil.

5. The method of claim 1, wherein the metal component comprises a copper seed, an aluminum seed, or an iron seed.

6. The method of claim 1, wherein the metal component comprises metal foil, and wherein the metal foil has a thickness at least four times the skin depth of the metal.

7. The method of claim 1, wherein the rewarming of the tissue is at a rate of at least 500° C./min.

8. The method of claim 1, wherein the metal component is a metal foam or metal foil and wherein inductively heating the metal foam or metal foil generates a specific absorption rate of 89 to 233 W/cm$^3$.

9. The method of claim 1, wherein the method further comprises tailoring the metal component to fit the tissue type.

10. The method of claim 1, wherein the biological tissue comprises an artery segment and the metal component comprises a foil, and wherein the contacting the biological tissue with the composition comprises, rolling the foil into a hollow cylinder and placing the hollow cylinder on an inside or outside surface of the artery segment.

11. The method of claim 1, wherein the metal component comprises a foil.

12. The method of claim 1, wherein the metal component comprises a seed.

13. The method of claim 1, wherein the electromagnetic induction field is induced by an induction coil.

14. The method of claim 1, wherein the metal component is not magnetic nanoparticles.

15. A method comprising:
    contacting a biological tissue with a composition comprising:
        a cryoprotective agent; and
        a metal component comprising a metal foam;
    cooling the tissue; and
    rewarming the tissue, wherein the rewarming comprises inductive heating of the metal foam.

16. The method of claim 15, wherein the metal component comprises a copper foam.

17. The method of claim 15, wherein the metal component comprises metal foam, and wherein the metal foam comprises at least 10 pores per inch (PPI).

18. The method of claim 15, wherein the metal component comprises metal foam, and wherein the metal foam comprises a porosity of from 0.89 to 0.97.

19. The method of claim 15, wherein the metal component comprises copper foam with a cylindrical shape.

20. The method of claim 15, wherein the metal foam comprises copper, aluminum, iron, or a combination thereof.

* * * * *